United States Patent
Monnier et al.

(10) Patent No.: US 6,881,851 B1
(45) Date of Patent: Apr. 19, 2005

(54) PREPARATION OF TETRAHYDRO-3-FUROIC ACID

(75) Inventors: John Robert Monnier, Kingsport, TN (US); Elaine Beatrice Mackenzie, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/828,728

(22) Filed: Apr. 21, 2004

(51) Int. Cl.⁷ .............................................. C07D 307/02
(52) U.S. Cl. ...................................... 549/486
(58) Field of Search ......................................... 549/486

(56) References Cited

U.S. PATENT DOCUMENTS 4,376,208 A * 3/1983 Vietti
5,789,416 A * 8/1998 Lum et al.
5,945,549 A * 8/1999 Beavers

OTHER PUBLICATIONS

M. Prashad et al., Synthetic Communications, 29(17), (1999), p. 2937–2942.*

V. Boekelheide et al., J. Am. Chem. Soc., 80, (1958), p. 3905–3907.*

* cited by examiner

*Primary Examiner*—Amelia Averill Owens
(74) *Attorney, Agent, or Firm*—Michael J. Blake; Bernard J. Graves, Jr.

(57) ABSTRACT

Disclosed is a process for the preparation of tetrahydro-3-furoic acid by the thermal, non-catalytic oxidation of 3-formyltetrahydrofuran using molecular oxygen.

7 Claims, No Drawings

PREPARATION OF TETRAHYDRO-3-FUROIC ACID

FIELD OF THE INVENTION

This invention pertains to a process for the preparation of tetrahydro-3-furoic acid by the oxidation of 3-formyltetrahydrofuran (3-FTHF). More specifically, this invention pertains to the preparation of tetrahydro-3-furoic acid by the thermal oxidation of 3-formyltetrahydrofuran using molecular oxygen. The oxidation process advantageously is carried out in the absence of a catalyst.

BACKGROUND OF THE INVENTION

The preparation of tetrahydro-3-furoic acid (3-THFA) has been reported in the literature. For example, the oxidation of tetrahydrofuran-3-methanol to 3-THFA using $NaIO_4$/$RuCl_3.H_2O$ in $H_2O/CH_3CN$ has been described by M. Prashad, et al., *Syn. Comm.*, 29(17), 2937 (1999). Another method reported by V. Boekelheide, et al., *J. Am. Chem. Soc*, 80, 3905 (1958) involves the skeletal reduction of 3-furoic acid. Because these known routes to 3-THFA involve chemical transformations of intermediates more complex and functionalized than 3-FTHF, there is a need to improve both the overall yield and economics of 3-THFA production.

BRIEF SUMMARY OF THE INVENTION

We have discovered that 3-THFA may be produced by heating 3-FTHF in the presence of a molecular oxygen-containing gas under elevated pressure in the absence of an oxidation catalyst. Thus, the present invention provides a process for the preparation of 3-THFA which comprises contacting 3-FTHF with a molecular oxygen-containing gas at a temperature of about 25 to 200° C. and a pressure of about 1.0 to 70 bars absolute in the absence of an oxidation catalyst. The process is advantageous since it is carried out in the substantial absence of an oxidation catalyst, i.e., in the absence of normal catalytic quantities of an oxidation catalyst. 3-THFA may be used as a co-monomer in the preparation of certain poly(ether-esters). 3-THFA also may be used in the preparation of certain adenosine derivatives as described in U.S. Pat. No. 5,789,416.

DETAILED DESCRIPTION

The oxidation process of the present invention provides a simple means for the conversion of 3-FTHF to 3-THFA in good conversion and yields. The starting material, 3-FTHF, may be obtained by the hydroformylation of 2,5-dihydrofuran according to known processes, e.g., the processes described in U.S. Pat. Nos. 4,376,208 and 5,945,549. The process normally is carried out in the presence of an inert solvent, i.e., a solvent in which both the reactant 3-FTHF and product 3-THFA are soluble. Examples of such solvents include inert, polar solvents such as water, C1 to C10 alkanols, C2 to C10 aliphatic and cycloaliphatic ethers, C2 to C10 glycols and C3 to C10 alkyl glycol ethers. The concentration of 3-FTHF in the inert solvent may range from about 1.0 to 90 weight percent, more typically about 5.0 to 80 weight percent, based on the total weight of the 3-FTHF and the solvent. An aqueous solution of 3-FTHF obtained as described in U.S. Pat. No. 5,945,549 is a convenient form of the 3-FTHF for use in the present invention.

The oxidation process is carried out by intimately contacting 3-FTHF, typically dissolved in an inert solvent, with a molecular oxygen-containing gas under oxidation conditions of pressure and temperature. The molecular oxygen-containing gas may be oxygen, oxygen diluted by an inert gas such as nitrogen, helium or other inert gas, air, or oxygen-enriched air. The thermal oxidation of 3-FTHF by molecular oxygen occurs readily at modest reaction conditions. The oxidation temperature may be in the range of about 25 to 200° C., preferably in the range of about 40 to 175° C. and most preferably in the range of about 60 to 150 C. The oxidation may be carried out at total pressures in the range of about 1 to 70 bar absolute (bara), preferably in the range of about 3.0 to 50 bara, and most preferably in the range of about 5.0 to 30 bara. The oxygen partial pressure normally is in the range of about 0.3 to 40 bara, preferably in the range of about 0.7 to 30 bara and most preferably in the range of about 1.0 to 25 bara. The oxygen partial pressure should, of course, be outside the flammability range in the particular solvent employed.

As noted above, the present oxidation process preferably is carried out in the absence of a catalyst, i.e., in the absence of catalytically effective amounts of a catalyst. The absence of a catalyst lowers the cost of the materials required for the oxidation process, reduces process costs by avoiding catalyst recovery or recycle, and results in higher selectivities to the desired reaction product, 3-THFA.

The oxidation process of the present invention may be carried out as a batch, continuous or semi-continuous process. Batch operation may be accomplished in an agitated pressure vessel, e.g., an autoclave, wherein a solution of 3-FTHF is fed to the vessel and a molecular oxygen-containing gas is fed to and maintained at an elevated pressure while the solution is agitated. Alternatively, the process may be carried out in a continuous manner by constantly feeding a solution of 3-FTHF and a molecular oxygen-containing gas to a reaction vessel operated at elevated pressure and temperature. A solution containing 3-THFA product is removed continuously from the reaction vessel and the product is isolated from the inert solvent, e.g., by distillation, extraction, or acid salt formation.

EXAMPLES

The operation of the process of the present invention is further illustrated by the following examples wherein all percentages given are by weight unless otherwise specified. The oxidation experiments were carried out in a stainless steel, 100 ml volume, high pressure autoclave reactor (Autoclave Engineers EZ-Seal) equipped with a high pressure gas manifold inlet system capable of adding oxygen-containing gas streams to the liquid phase reaction medium. The gas stream was added below the liquid level within the reactor near the impeller/stirrer. The stirrer was maintained at 1500 RPM to ensure rapid and even mixing of the oxygen-containing gas stream with the liquid 3-FTHF/solvent medium within the reactor. In order to maintain constant pressure within the reactor body, a high pressure, total reflux column served to vent the gas stream from the reactor body. A back pressure regulator was used to maintain the overall reactor pressure at the desired pressure. The 3-FTHF solution was added to the solvent and oxygen-containing gas stream of the autoclave by means of a high pressure syringe pump to initiate the thermal oxidation reaction. Microliter-sized samples of the liquid phase reaction medium were taken at different time intervals by means of a capillary dip tube maintained in the liquid level of the reactor.

In a typical experiment, the reactor was charged with 40 g of water and 12 drops of an internal GC standard, tetramethylene sulfone, and sealed. The desired gas phase composition of oxygen with optional inert gas diluent was flowed through the reactor and the desired reaction pressure set using the back pressure reactor at the exit of the reflux condenser. The reactor was then heated to the desired reaction temperature using a band heater tightly wrapped around the exterior of the reactor body. The stir rate of the solution was set at 1500 RPM to ensure rapid and uniform mixing at all reaction conditions. The pressure was raised to 8.6 bara (125 pounds per square inch—psia) using a predetermined gas flow composition of $O_2$ and He to give the desired $O_2$ partial pressure. Constant pressure was maintained in the autoclave reactor by the back pressure regulator after the gaseous reactor effluent was cooled to 2° C. in a total reflux-type of stainless steel coiled condenser.

After the reactor was heated to the desired temperature, 10.0 g of a 50% solution of 3-FTHF in water quickly was added at high pressure through the syringe pump into the reactor to give a total volume of approximately 50 mls solution, which defined time=0 for the kinetic experiments. Each reaction typically was run for 5 to 6 hours, samples were taken periodically using the dip tube in the reactor and were subsequently analyzed by gas chromatography (GC). In one experiment, off gases were collected in a gas sample bomb and analyzed for $CO_2$ using a different GC, which had been calibrated for $CO_2$. Negligible amounts of $CO_2$-were observed at all reaction times, confirming that combustion of feed and product were not occurring during the thermal oxidation reaction.

Example 1

3-FTHF was oxidized over a period of 5 hours at 100° C. and 8.6 bara (125 psia) overall pressure (5.0 bara {72.5 psia} $O_2$ and 3.6 bara {52.5 psia} He) according to the procedure described above. The course of the reaction was observed by periodically sampling the reaction mixture and analyzing for 3-FTHF. The results are shown in Table I wherein Time is the time (minutes) of the reaction measure as described above and 3-FTHF is the normalized micromoles of unreacted 3-FTHF present in the reaction mixture.

TABLE I

| Time | 3-FTHF |
| --- | --- |
| 0 | 100 |
| 5 | 100 |
| 10 | 90.4 |
| 20 | 70.7 |
| 40 | 44.7 |
| 60 | 35.0 |
| 90 | 24.9 |
| 120 | 19.0 |
| 180 | 12.3 |
| 240 | 8.4 |
| 300 | 7.2 |

Example 2

The procedure of Example 1 was repeated except that after 150 minutes of reaction time of a second aliquot of 10.0 grams of 50% aqueous 3-FTHF solution was pumped into the autoclave reactor. The course of the reaction was observed by periodically sampling the reaction mixture and analyzing for 3-FTHF. The results are shown in Table II wherein Tim is the time (minutes) of the reaction measured as described above and 3-FTHF is the normalized micromoles of unreacted 3-FTHF present in the reaction mixture.

TABLE II

| Time | 3-FTHF |
| --- | --- |
| 0 | — |
| 5 | 129.9 |
| 10 | 130.0 |
| 20 | 118.0 |
| 40 | 74.9 |
| 60 | 55.7 |
| 90 | 42.4 |
| 120 | 29.7 |
| 150 | 23.3 |
| 160 | 154.2 |
| 170 | 166.5 |
| 190 | 125.4 |
| 210 | 84.6 |
| 240 | 57.7 |
| 270 | 45.8 |
| 300 | 32.0 |
| 330 | 25.0 |
| 360 | 19.0 |
| 390 | 14.8 |

Examples 3–5

The procedure of Example 1 was repeated using different reaction temperatures as shown in Table III wherein Temp is the temperature (° C.) at which the experiment was carried out and Time has the meaning given above in Example 1. In these examples, the $O_2$ pressure was maintained constant at 8.6 bara (125 psia) at a total reaction pressure of 8.6 bara1(25 psia). The samples taken periodically were analyzed for 3-FTHF and 3-THFA. Table III also reports the Conversion of 3-FTHF and the Selectivity to 3-THFA at each point of Time. Conversion is the percent conversion of FTHF to all products:

$$\frac{\text{Moles 3-}FTHF \text{ converted to products}}{\text{Moles 3-}FTHF \text{ initially present}} \times 100.$$

Selectivity is the percent selectivity to THFA defined as $$\frac{\text{Moles 3-}FTHF \text{ converted to 3-THFA}}{\text{Moles 3-}FTHF \text{ converted to all products}} \times 100.$$

TABLE III

| Example | Temp | Time | Conversion | Selectivity |
| --- | --- | --- | --- | --- |
| 3 | 68 | 10 | 30 | >99 |
| 3 | 68 | 60 | 32 | 99 |
| 3 | 68 | 150 | 37 | 99 |
| 3 | 68 | 392 | 44 | 99 |
| 4 | 100 | 10 | 22 | >99 |
| 4 | 100 | 60 | 70 | 94 |
| 4 | 100 | 150 | 87 | 91 |
| 4 | 100 | 300 | 94 | 86 |
| 5 | 125 | 10 | 64 | 98 |
| 5 | 125 | 60 | 97 | 79 |
| 5 | 125 | 150 | 99 | 76 |
| 5 | 125 | 240 | 100 | 79 |

Examples 6–8

The procedure of Example 1 was repeated at 100° C. and 8.6 bara (125 psia) overall pressure except that different oxygen partial pressures were used as shown in Table IV wherein O₂ Press is the oxygen partial pressure (bara—psia) at which the experiment was carried out and Time has the meaning given above in Example 1. The samples taken periodically were analyzed for 3-FTHF and 3-THFA. Conversion and Selectivity have the meanings provided in Examples 3–5.

TABLE IV

| Example | O₂ Press | Time | Conversion | Selectivity |
|---------|----------|------|------------|-------------|
| 76 | 1.9–27.5 | 10 | 11 | >99 |
| 6 | 1.9–27.5 | 60 | 59 | 88 |
| 6 | 1.9–27.5 | 150 | 86 | 85 |
| 6 | 1.9–27.5 | 300 | 94 | 81 |
| 7 | 5.0–72.5 | 10 | 7 | >99 |
| 7 | 5.0–72.5 | 60 | 46 | >99 |
| 7 | 5.0–72.5 | 150 | 84 | 96 |
| 7 | 5.0–72.5 | 300 | 94 | 91 |
| 8 | 6.9–100 | 10 | 22 | >99 |
| 8 | 6.9–100 | 60 | 70 | 94 |
| 8 | 6.9–100 | 150 | 87 | 91 |
| 8 | 6.9–100 | 300 | 94 | 86 |

Example 9

The basic procedure of Example 1 was repeated except that the starting material was 75 g of a 50% aqueous 3-FTHF solution and the oxidation was carried out over a time of 3 hours. The results are shown in Table V wherein Time, Conversion and Selectivity have the meanings provided in the preceding examples.

TABLE V

| Time | Conversion | Selectivity |
|------|------------|-------------|
| 20 | 23 | 92 |
| 40 | 38 | 90 |
| 120 | 76 | 80 |
| 180 | 92 | 78 |

The invention has been described in detail with particular reference to preferred embodiments thereof, but it will be understood that variations and modifications may be effected within the spirit and scope of the invention.

We claim:

1. Process for the preparation of tetrahydro-3-furoic acid which comprises contacting 3-formyltetrahydrofuran with a molecular oxygen-containing gas at a temperature of about 25 to about 200° C. and a pressure of about 1.0 to about 70 bars absolute in the substantial absence of an oxidation catalyst.

2. Process according to claim 1 wherein the process is carried out in the presence of an inert solvent at a temperature of about 40 to about 175° C. and a pressure of about 3.0 to about 50 bars absolute.

3. Process according to claim 1 wherein the process is carried out at a temperature of about 40 to about 175° C. and a pressure of about 3.0 to about 50 bars absolute in the presence of an inert, polar solvent selected from water, C1 to CIO alkanols, C2 to C10 aliphatic and cycloaliphatic ethers, C2 to CIO glycols and C3 to C10 alkyl glycol ethers.

4. Process according to claim 1 wherein the process is carried out at a temperature of about 40 to about 175° C. and a pressure of about 3.0 to about 50 bars absolute using a solution of 3-formyltetrahydrofuran in water wherein the concentration of 3-formyltetrahydrofuran is about 5 to about 80 weight percent.

5. Process according to claim 1 wherein the process is carried out at a temperature of about 60 to about 150° C. and a pressure of about 5.0 to about 30 bars absolute in the presence of an inert, polar solvent selected from water, C1 to C10 alkanols, C2 to C10 aliphatic and cycloaliphatic ethers, C2 to C10 glycols and C3 to C10 alkyl glycol ethers.

6. Process according to claim 1 wherein the process is carried out at a temperature of about 50 to about 150° C. and a pressure of about 5.0 to about 30 bars absolute using a solution of 3-formyltetrahydrofuran in water wherein the concentration of 3-formyltetrahydrofuran is about 5 to about 80 weight percent.

7. Process according to claim 1 wherein the process is carried out at a temperature of about 50 to about 150° C. and a pressure of about 5.0 to about 30 bars absolute using a solution of 3-formyltetrahydrofuran in water wherein the concentration of 3-formyltetrahydrofuran is about 5 to about 80 weight percent and the molecular oxygen-containing gas is oxygen, oxygen diluted by an inert gas, air or oxygen-enriched air.

* * * * *